United States Patent [19]

Bullock et al.

[11] 4,123,173

[45] Oct. 31, 1978

[54] ROTATABLE FLEXIBLE CUVETTE ARRAYS

[75] Inventors: Frederick C. Bullock, Towaco, N.J.; Alvin Engelhardt, Nanuet; Thomas J. Cirincione, Flushing, both of N.Y.; Joseph A. Williams, Wayne, N.J.

[73] Assignee: Electro-Nucleonics, Inc., Fairfield, N.J.

[21] Appl. No.: 694,303

[22] Filed: Jun. 9, 1976

[51] Int. Cl.² ............................................. G01N 1/10
[52] U.S. Cl. .................................. 356/246; 356/197; 422/64; 422/100
[58] Field of Search ...................... 356/196, 197, 246; 250/231 SE; 23/253 R

[56] References Cited

U.S. PATENT DOCUMENTS

| 3,441,383 | 4/1969 | Moore et al. | 23/259 X |
|---|---|---|---|
| 3,532,470 | 10/1970 | Rochte | 23/253 R |
| 3,532,470 | 10/1970 | Rochte | 23/253 R |
| 3,555,284 | 1/1971 | Anderson | 23/259 |
| 3,679,129 | 7/1972 | Livshitz et al. | 23/259 X |
| 3,759,666 | 9/1973 | Hill, Jr. | 23/259 X |
| 3,804,533 | 4/1974 | Scott | 356/246 X |
| 3,811,780 | 5/1974 | Liston | 356/246 X |
| 3,829,223 | 8/1974 | Hamel | 356/246 |
| 3,854,508 | 12/1974 | Burtis et al. | 23/259 X |
| 3,856,470 | 12/1974 | Cullis et al. | 23/259 X |
| 3,873,217 | 3/1975 | Anderson et al. | 356/246 |
| 3,890,101 | 6/1975 | Tiffany et al. | 35/246 |
| 3,986,534 | 10/1976 | Schmidt | 23/253 R X |

Primary Examiner—John K. Corbin
Assistant Examiner—Matthew W. Koren

Attorney, Agent, or Firm—Cooper, Dunham, Clark, Griffin & Moran

[57] ABSTRACT

A disposable flexible disc radial cuvette array has its cuvettes divided into inner compartments and outer compartments by a ramp-shaped wall. These cuvettes are separated from their adjacent cuvettes by dual side walls and have uniform parameters. The annular cuvette array includes an integral opaque horizontal annulus having a first radial series of slots thereon, substantially aligned with the radial centers of the outer ends of the cuvettes, and has a second radially spaced set of slots generally aligned with the side walls. The cuvette walls and array hub portion provide rigidity. The annulus also has an inwardly extending flange covering the outer radial ends of the cuvette, there being formed therein slots open to both the inner and outer compartments. Locating projections extend upwardly from the disc surface in an embodiment adapted to position a rotatable, cuvette numbering, annular ring, the ring being variably, rotatably positionable to provide selectivity of the cuvette numbers. The thickness of the plastic material forming the array is selected empirically for proper optical and strength characteristics. The array is flexible and integrally spring biased between hub and annulus to maintain the bottom walls of the cuvettes against the rotatable support with which the cuvette array is to be utilized under pressure to maximize contact therebetween. The annulus is fusion bonded to the hub and cuvette chamber portion to form the integral array.

13 Claims, 16 Drawing Figures

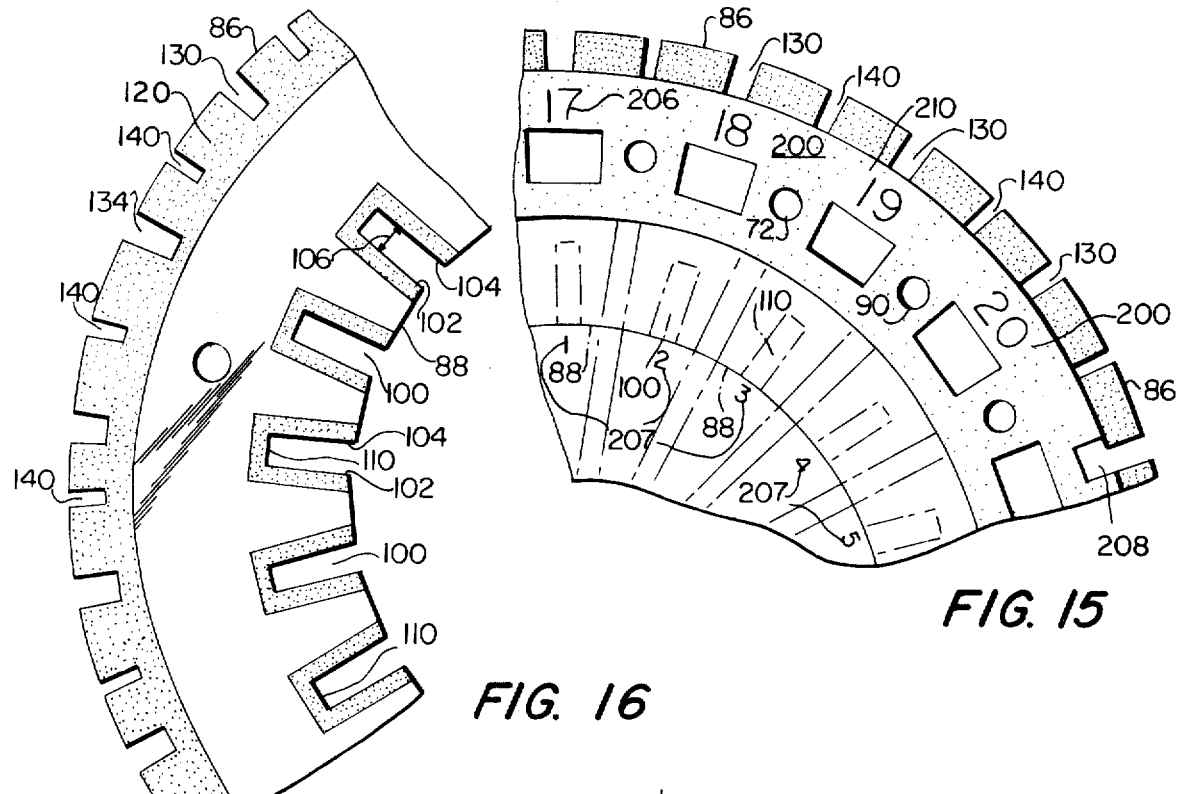
FIG. 15
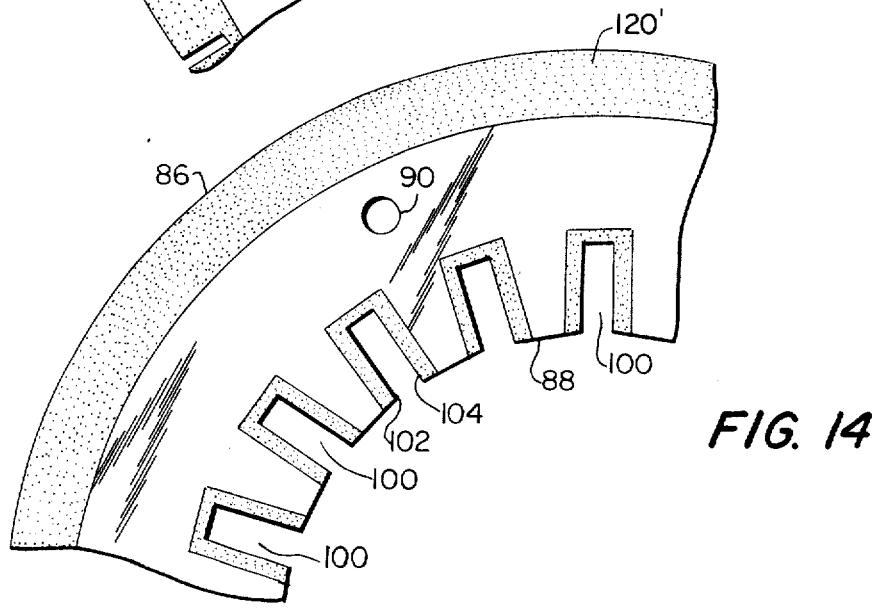
FIG. 16
FIG. 14

ROTATABLE FLEXIBLE CUVETTE ARRAYS

BACKGROUND OF THE INVENTION

This invention relates generally to rotatable disc cuvette arrays and assemblies adapted for use in a centrifugal fast analyzer having means to centrifugally rotate the array in order to produce measurements of the optical density or absorbance values of a light path passing successively through each of a series of radially spaced cuvettes during their rotation. Such systems are in wide use, particularly for absorbance measurements utilized with analytical apparatus.

More specifically, these fast analyzers are generally furnished with an array usually having individual inner and outer compartments for each of the cuvettes. These compartments are physically separated from each other by a wall such as an annular ramp which divides each cuvette into these inner and outer compartments and prevents fluid communication therebetween prior to centrifugation. Such arrays have a structure wherein a central hub portion has positioned outwardly thereof a selected number of radially disposed cuvettes. Normally each of the individual cuvettes are radially positioned side by side and have a common radially extending dividing wall between each pair of adjacent cuvettes to form the disc portion of the assembly into the rotatable cuvette array. The inner compartments usually comprise a holding means for whatever reagents or reactants which are placed therein prior to the centrifugation run and read cycle. The outer compartments are also formed into an annular ring, spaced radially outward from the inner compartments, and are divided therefrom prior to centrifugation by the described wall or walls, preferably ramp-shaped in form and having an inner vertical wall which preferably has an inclination in the vertical plane of approximately 40° to 60° degrees, so as to form the desired ramp angle between the inner and outer compartments.

Such rotary cuvette assemblies are particularly adapted for use in a clinical analyzer in their most common useage, in order to produce a reaction between the material contained within the inner compartment and that material which is contained in the outer compartment, the latter usually comprising an unknown sample, for example, a body fluid. The most common use of these analyses is the determination of blood or blood plasma or serum components, the blood forming the sample, or unknown, material under test and being deposited in the outer ring of compartments. Upon centrifugation the reagent or reactant materials contained in the inner compartments, diluted if desired to a fixed concentration and/or pH, are thrown outwardly and rise over the inner inclined walls or ramps of the cuvette compartment dividers and then flow into the outer chambers where they intimately contact and mix with the materials contained in the chambers. Typically, the parameters of the blood or other material contained in the outer compartments, as well as those of the materials contained within the inner compartments, are carefully fixed as to volume, temperature, acidity, etc., and have been treated prior to use for removal of fibrins or similar debris which would have an adverse effect upon the reaction and upon the uniformity and light tramsmission characteristics of the measured optical density of the materials when they become mixed in the outer compartments. In many instances in the prior art there has been used an assembly of rotary cuvettes which is provided with an additional radially aligned chamber, or compartment, for each of the individual cuvettes, the third compartments being spaced radially outwardly from the second compartments, so as to form a third annular ring of compartments. Where this is done, an additional annular compartment separating or partition wall, which may also be of the slope or ramp type, provides the separation means between the second annular series of cuvette compartments and the outermost third series of compartments of the overall assembly. In this latter type of prior art three-compartment duvettes, the reaction takes place for the most part in the third compartment, although in some analytical or other reactions a portion of the reaction will occur while the materials from the first, most inwardly positioned compartments are flowing in partially mixed form with the materials from the second compartments prior to the combined flow reaching the third compartments.

Although the centrifugation speeds generally used with such analyzers, particularly for clinical analysis, are not of such great magnitude as to fall within the ultra centrifugation range of 20,000 rpm or more, the usual fast analyzer rotor speed is sufficient so that the mixed materials will generally be centrifugally forced into a vertical layer against the outer vertical walls which form the final vertical wall of the overall cuvettes. Preferably, as stated above, the cuvettes are physically made as identical as is possible in so far as each component part thereof is concerned.

In order to avoid spillage, or to minimize the possibility of spillage of the materials during the run, the heights of the dividing ramps are so selected relative to the greater height of the radial walls which divide the cuvettes from each other, and which form the side walls of each of the compartments of the cuvettes, that such spillage is avoided without undue interference with the travel of the materials to their most radially outward position, where the components from the inner compartments are mixed and form a substantially vertical layer against the vertical outer wall of each of the cuvettes. During the centrifugal run the cover seal and the joints between the parts are subjected to the greatest forces tending to cause spillage or leakage.

For details of the use of such apparatus, and disclosures of various processes which can be carried out thereby, reference is made to the following patents which disclose such curvette arrays utilized in a clinical, electronically corrected, interfaced fast analyzer, generally known as small or miniature fast analyzers, such apparatus and systems originally having been developed for the most part by the Oak Ridge National Research Laboratory of the Nuclear Regulatory Commission of the Energy Research Development Agency, this commission formerly being known as the United States Atomic Energy Commission, and the original large scale analyzers produced thereby having been known as GeMSAEC analyzers: Norman G. Anderson Pat. Nos. 3,536,106, 3,547,547, 3,555,284, 3,582,218, 3,586,484, 3,798,459; Mailen U.S. Pat. No. 3,744,975; Tiffany el al., U.S. Pat. No. 3,763,374; Scott et al., U.S. Pat. No. 3,800,161; Mullaney et al., U.S. Pat. No. 3,824,402; Hinman, U.S. Pat. No. 3,863,049.

Additionally, details of such prior art structures and processes for using the same are shown and described in detail in many literature references including the following: *Basic Principles of Fast Analyzers* (1971) Amer. J. Clin. Path., Vol. 53, pp. 778-785, by Norman G. Anderson; *Computer Interfaced Fast Analyzers* (1969)

Science, Vol. 166, pp. 317-324, by Norman G. Anderson; *Increased Rate of Analysis by Use of a 42-Cuvette GeMSAEC Fast Analyzer* (1971) Clinical Chemistry, Vol. 17, pp. 686-695, by Burtis et al., *Dynamic Introduction of Whole-Blood Samples into Fast Analyzers* (1972) Clinical Chemistry, Vol. 18, pp. 749-752, by Scott et al.; *Development of a Portable Data Processer With Mechanical Data Output for Use With a Miniature Fast Analyzer* (1972) Clinical Chemistry, Vol. 18, pp. 762-770, by Johnson et al.; *Development of an Analytical System Based Around a Miniature Fast Analyzer* (1973) Clinical Chemistry, Vol. 19, pp. 895-903, by Burtis et al.; *A Miniature Fast Analyzer System* (1973) Analytical Chemistry, Vol. 45, pp. 327A-340A, by Scott et al.; *Optimization* and *Analytical Application of the Technique of Dynamic Introduction of Liquids into Centrifugal Analyzers* (1974) Clinical Chemistry, Vol. 20, pp. 932-941, by Burtis et al.; *A Centrifugal Analyzer With a New All-Digital Measurement System* (1974) Clinical Chemistry, Vol. 20, pp. 942-949, by Avery et al., *Incorporation of a High-Speed Decimal Data Processor Into a Centrifugal Analyzer* (1974) Clinical Chemistry, Vol. 20, pp. 950-960, by Gregory et al.; *A Small Portable Cenntrifugal Fast Analyzer System* (1974) Clinical Chemistry, Vol. 20, pp. 1003-1008, by Scott et al.; *Blood Grouping with a Miniature Centrifugal Fast Analyzer* (1974) Clinical Chemistry, Vol. 20, pp. 1043-1057, by Tiffany et al.; *Programming Concepts for the GeMSAEC Rapid Photometric Analyzer,* (1974) Clinical Chemistry, Vol. 20 by Kelley et al.

In general, the prior art cited above has utilized a multi-cuvette array which essentially consists of an array composed of a plurality of pie-shaped, radially disposed cuvettes which radiate out from a central hub portion and which contain in radial order in each of the chambers or cuvettes, proceeding radially outwardly from the hub or center of the generally round, substantially disc-shaped array structure: a first annular series of chambers for initially holding a first group of reactants, an annular series of dividing walls or ramps, one for each cuvette, a second annular series of compartments for holding initially different reagents which frequently are the unknown samples of blood or other body fluids, and an outer annular series of vertical end walls.

It has generally been convenient in this prior art to form such discs with the individual cuvettes thereof being integrally united at the time of manufacture. During the reacton run the array is rotated at a speed to cause the contents of the first chambers to climb over the ramps under centrifugal force and mix and react with the materials contained in the second chambers.

On top of the cuvettes there are generally placed some form of cover means to prevent evaporation and contamination, the cover means still leaving paths for the measurement of the optical density or fluorescent emission characteristics of the reacting materials, when the array is rotated, with these openings, one for each cuvette, passing between a source of illumination, in the case of measurement of absorption, and an optical light transmission sensing means. The disc array is usually driven at speeds of between about 300 and about 500 rpm during most of such measurement run cycles after a preliminary initial fast run at higher speeds in the vicinity of 3,000 to 5,000 rpm to cause more rapid initial reaction by increasing initial reactant material contact.

The chamber in which the cuvette and other apparatus is placed and/or the cuvette array itself has its temperature controlled closely, usually by heating during an incubation period both prior to and during this run in which the reaction is occurring. The light transmission characteristics are changing as the reaction proceeds and, since the temperature affects this rate, it must be accurately controlled.

Because of the necessity for extremely accurate measurements, it is essential that all of the components of the overall fast analyzer possess parameters which should be determined with as high a degree of accuracy as possible. This desired accuracy necessity is disclosed in the above cited patents and literature references and the reasons therefor are discussed at length therein.

Even though the reactants placed in each cuvette total only small amounts measured in microliters, in the ideal, optimum, analytical systems each component of the system, including the entire optical system, the rotation motor drive speed, the means for holding the rotor, as well as the cuvette array, are all accurate to within less than 0.1 percent variation. To ensure the repetitive accuracy of the readings of the optical density through the cuvettes, it has therefore been the object of the prior art to define in the disclosed systems an apparatus in which the individual cuvettes of the array are made as identical as is possible as to parameters from cuvette-to-cuvette; and all of the parts, including the cuvette array are fixed so that minimal error variations are introduced. In order to accomplish this desired result the prior art has generally relied upon expensive cuvette array discs which are close tolerance machined in order to ensure maximum uniformity. Plastic materials of proper optical density have been suggested in the above prior art, but such systems have used, of necessity, rigid, thick plastic plates in order to be able to accurately tool-machine these plates so as to form them with the chambers and optical passages as finished components which are then assembled into a unitary cuvette array structure by means of multiple clamping plates and sealing or the like plates, into a complex multiple part assembly.

These prior art devices have usually included a solid opaque cover plate positioned over the entire array, except for an annular series of radially disposed passageways through the top cover immediately above the first or inner annular series of chambers of the cuvettes and a similar annular series of openings positioned above the second radially outwardly positioned annular series of chambers of the cuvettes. Such holes are generally relatively small and are positioned over the approximate radial centers of each of the cuvettes relative to the side walls thereof so as to provide passages for placing the materials in the chambers.

In order to ensure that the clamping ring and the plates which make up the assemblies are accurately aligned, it has been a common expedient to use mating indexing vertical protrusions on the components, so that these vertical indexing projections will coact when assembly occurs, fixing the elements spatially relative to each other.

It is most desirable during the absorbence run that additional means be provided whereby the reading of the optical density of the cuvettes is accomplished for each cuvette at a fixed radial position, such position generally having been chosen at or near the exact center of the arcuate outer end wall of each cuvette. Also, it is desirable, if not essential, to provide each of the cuvettes with some identification means, such as numbers therefor, which enables the users thereof to program an electronic readout system and digital computer, or to program the electronic interfacing means for coaction with the computer, so as to identify the readings by cuvette number, such number identification of each cuvette being utilized with an automatic printout mechanism, all as described in the above references.

While various means for providing for such cuvette indentification and for the timed reading thereof have been used in the past, the most commonly used system is one in which the rotor holder for the cuvette array has positioned thereon, or associated physically therewith, some form of encoding system, which may consist of an optically transmissive annular series of slots, each of which is positioned opposite the center of each cuvette when the cuvette is aligned in, and supported by, the rotor holder. This series of indexing slots or other such means may be used to locate the particular cuvette area which is being measured; i.e., which is passing through the main optical path during the rotation of the run cycle. Alternatively suggested by the prior art have been systems incorporating a second disc mounted on the rotor shaft, this second disc having optical passageways, or magnetic markings, aligned with the cuvettes thereabove. There have also been suggested systems in which reflectors have been used for the encoding or position-identifying means. Such systems have invariably been either inaccurate or very elaborate as to their structure. Furthermore, such misalignment as is present will be repeated for each cuvette; i.e., if the rotor holder or second disc are angularly displaced five degress relative to the cuvettes of the disc, then each cuvette chamber will be displaced 5°, resulting in totally inaccurate readings. It has, therefore, been recognized by the prior art workers that it would be ideal if the cuvette array utilized in the system could be made more accurate, less complex and less expensive by using inexpensive materials and methods of manufacturing, eliminating the machine tooling used by the prior art in order to provide structures possessing reproducibility sufficiently accurate for each analytical run. These prior art workers have also emphasized that it is essential, in order to obtain adequately accurate readings, that these parts, even after initial accurate alignment, must not move relative to each other during the entire centrifugation, from the inception to the completion of the analytical run, in order to avoid the introduction of new errors resulting from such relative displacement of the parts.

The prior art workers have mentioned also the desirability of the use of disposable, less expensive cuvette arrays, but have stated that this is not possible, because the disclosed prior art systems could not utilize such simple, inexpensive, disposable array and still provide the essential accurate stability of measurements which is required. This has been emphasized as to impracticality when it is realized that the microliter amounts of reagents used in the overall systems of such analyzers must have optical density cyclical measurements thereof determined by mechanical and electrical means which will produce a final series of electronically corrected signals from the computer to a printing mechanism, for which corrections should have been made for each of the following possible sources of errors: cuvette-to-cuvette non-uniformity as to size, radial or axial positioning, or thickness of the radiation permeable walls (e.g., non-uniform light transmission characteristics), variance in the intensity of the light source illuminating the optical path which the cuvettes intercept during reading, variation in the length of this optical path, non-uniform pulse reading times, programmed changes in rotor speed, radial displacement of the entire disc and rotor relative to the optical path, inherent variations in the rotor speed caused by changes in the voltage supplied to the motor drive of the rotor, non-uniform gain control of the electronic components, radial displacement of the positioning of the rotor holder relative to the cuvette array, random movement of the materials which react within the individual cuvettes during the run and read cycle, variations in the temperature and other environmental characteristics which cause differential expansion of the cuvette array and the rotor and cause changes in the reaction rate under which the analyses are performed, a high background noise to optical density ratio, as well as voltage or other variations in these correcting systems, and correction means for error compensation which are caused by either too rapid correction or slow reaction so that hunting will occur when the correction means operate. These systems of the prior art have, therefore, been non-accurate.

It is, therefore, a principle object of the present invention to provide inexpensive, disposable, rotatable cuvette array structures of generally disc-shaped, annular form, Which are much less expensive than any of those suggested in the prior art, and at the same time automatically eliminate a number of the above described errors inherent to the prior art, thereby reducing the complexity of the necessary prior art eleborate correction systems, so that the final system readout of the analytical run is more accurate than is possible with the prior art systems, even though it is much less complex in array structure.

Such results are obtained by the provision of unique structures including a number of unique, coating components of the rotary disc array.

It is, hence, an object of the invention to provide such an inexpensive, rotary cuvette array which provides at least as great accuracy as the previously known systems, and generally provides much greater accuracy, by the provision of geometrical fixation of previously known error sources by the spatially fixed relation of the various array components and including their configuration. Various modifications of sealing means for the cuvette are disclosed.

While the machine, system, and process described in the aforesaid applications in detail are the preferred overall systems in which the cuvette arrays of the present invention may be utilized, it is to be understood that, with very minor or with no alterations, the particular structures described and claimed in detail herein are capable of adaptive usage in many of the prior art systems.

SUMMARY AND OBJECTS OF THE INVENTION

A rotatable cuvette array for use with so-called fast anlyzers of the centrifugal type is described in various embodiments in all of which the array is disposable.

In a presently preferred embodiment, the array consists of a series of radially spaced, pie-shaped cuvettes, preferably formed by sheet molding, extending from a hub or center portion. The cuvettes are separated from each other by side walls which are preferably double thickness with a space between the two layers thereof. The cuvettes are divided radially into an inner and an outer series of side-by-side compartments. Each inner compartment is divided from each outer compartment for each cuvette by a division wall which is preferably ramp-shaped on its radially inward wall, so that this inner wall thereof is inclined vertically, angularly upward, while the outer wall thereof is inclined downward at a sharp vertical angle which may, in fact be 90 degrees. The ends of each of the outer compartments have inwardly or reverse curved side walls to direct the fluids during centrifugal motion toward the cuvette centers so as to increase the vortexing or swirling and, hence, to promote intimate mixing. The center portion of the outside wall of each outer compartment is a substantially vertical wall, which may be inclined at a slight angle to the vertical plane and which forms the wall against which the centrifuged materials are held by centrifugal force during rotation in a vertical fluid layer.

There is preferably formed a horizontal annular flange at the outer extremity of the integral plastic member forming this cuvette part of the structure. Circumferentially bonded thereto is a preferably flexible horizontal annulus formed of thin plastic material, having the desired light transmissive properties, and which overlies the cuvette end walls and is provided on the portion thereof beyond the end walls with a first series of slots which serve as encoding means, the slots having their edges radially aligned approximately with one edge of the associated cuvette. These slots are substantially rectangular in their preferred form. Substantially aligned with the cuvette radial division walls are a second series of slots, one for each division wall, these slots being also part of the encoding system and being used to provide for a zero referencing of the reading of each cuvette during the optical density analytical measurement. This portion of the annulus beyond the outer walls which contains the slots is made opaque by painting or the like. Extending radially inwardly there is formed an additional portion of the annulus which is substantially transparent optically across the portion thereof which covers the outer ends of the outer compartments of each of the cuvettes. The innermost part of the annulus is provided with lengthy slots therein extending horizontally beyond both walls of the ramp, so that these slots form access passage to each inner and outer compartment of each cuvette. Alternatively, a single opening may be formed for each cuvette just beyond the dividing ramp wall so as to provide a means of access to the outer compartments of the cuvettes. For ease of visual location, the edges of the slots or holes are surrounded by an opaque material.

There is an integral, thin plastic horizontal center hub portion from which the cuvettes radiate, each cuvette having its inner wall formed as a part of the hub vertical wall with the bottom of the hub wall extending vertically downward and inclined forward radially to aid in directional fluid flow. The hub may have a recessed or otherwise configured form to index the hub in a fixed position relative to the rotary carrier therefor during centrifugation.

The reverse curvature, outer compartment, walls form a series of annularly spaced notches or indentations which, in addition to controlling the flow of fluid or reagents or reactants placed in the inner and the outer compartments enable accurate alignment of the cuvette array disc with a rotor adapted to hold the array during the centrifugation. A rotary carrier is formed with a series of annularly spaced projections which have a shape and size such as to closely fit the notches when the array is positioned thereon.

Projecting upwardly from the walls of these notch members are one or more sets of protrusions spaced the same distances radially outwardly, this spacing being 180 degrees apart where they number only two, ninety degrees apart where the projections number four, 45 degrees apart where they number eight, etc. If desired, there may be such a projection or protrusion formed at each notch. This enables any one of a plurality, or all, of the individual cuvettes to be used as the reference cuvette, which is generally numbered one or which has no number.

The means by which this selectable, numbering identification of cuvettes is accomplished is a separate, opaque ring of generally flat shape having positioned therein a radial series of substantially rectangular openings, which openings will optically mate and align with the outer portions of the outer compartments positioned beyond the points of curvature, which portions pass through the optical path during reading. This ring bears a locating arrow and has cuvette numbers thereon, one number being opposite each of the optical openings and aligned with the cuvette. Between the openings there is provided in the ring a series of apertures each of which has a size slightly larger than the projections, so that they fit thereover in close, mating, coacting spatial relation. By rotating the ring prior to its seating on the upper annulus wall, any one of its apertures may be made to mate with the projection of any selected cuvette where each cuvette has a projection so that selection of the number one cuvette may be chosen at will.

Preferably, the cuvette array including the hub portion and the inner and outer compartments and notches and flange, the dividing side walls, the dividing compartment ramp walls and the projections are all formed from a single piece of thin, flexible plastic which is substantially transparent and which has a high degree of flexibility. The described configured structure may be performed in a single molding operation, such as pressure sheet shaping, and the necessary strength or rigidity is provided by the dual folded side walls, the dual inner and outer compartment walls, the end walls, the curved walls and other side wall ridges, if desired.

During the molding or shaping the material at the center is forced downwardly so that the hub portion is vertically, integrally biased below the outermost ring adjacent the notches and end walls. This causes the thin plastic material to be biased downward against any force attempting to raise the hub portion relative to the outer edges, providing these edges are fixed in space relative to the hub.

The plastic material is so selected that it will have sufficient flexibility and heat and light transmission characteristics, while remaining sufficiently rigid during use. This will vary according to the composition of the plastic material.

The annulus carrying the opaque encoding slots is preferably fusion bonded to a thin, relatively narrow outer annular flange positioned beyond the cuvette end walls. It serves in coaction with a centrally positioned cover member substantially sealing the cuvettes from the atmosphere.

It is a further object of the invention to enable the same cuvette array to be used for more than one centrifugal analytical run. Often only a few cuvettes, such as four in number, plus the reference cuvettes, are used, because only four tests are to be run. In the prior art structures, the entire cuvette array had to be thoroughly cleaned of contaminants just as if all the cuvettes has been utilized. With the structure of this invention, a five cuvette run is made, after which the indexing disc is elevated off the projections and rotated, for example, 180°, following which it is repositioned on the cuvette disc array by registered lowering onto the projections, so that a new series of cells, starting with a new reference cuvette may be utilized to make a new analytical run before discarding the disposable disc cuvette array.

The above described cuvette array and its encoding means are geometrically, spatially fixed, so as to eliminate many of the possible prior art errors while providing signals which control the speed of rotation of the array, locate and identify selectively the first cuvette, at which the optical density readings are taken to enable determination of chemical analysis and to provide an accurate, constant zero light transmissive reference level for each cuvette.

Thus in brief summary, the invention broadly involves a cuvette array for a centrifugal analyzer, in which the array comprises a plurality of compartments circumferentially spaced about a central point, which array is disposable and is formed from upper and lower discs of flexible thermoplastic material, the lower disc being formed with the compartments and the upper disc being bonded to the lower disc and closing off at least a portion of each of the compartments.

Additional objects and features of the invention will be apparent from the following descriptions of the preferred embodiments set forth in detail and taken in conjunction with the accompanying drawings and the appended claims.

BRIEF DESCRIPTION OF THE DRAWINGS

FIG. 14 is an enlarged plan view of a different embodiment in which there are no encoder rim slots.

FIG. 15 is an enlarge plan view of the cuvette array of FIG. 12 having been displaced 90° from its position in FIG. 12, so that an unused set of cuvettes from the first run are usably identified for a second run.

FIG. 16 is an enlarged plan view of a portion of a different embodiment wherein only one of the run encoder slots opposite the cuvette chambers is elongated, so that no indexing ring is required.

DETAILED DESCRIPTION OF THE PREFERRED EMBODIMENTS

Figure 1:
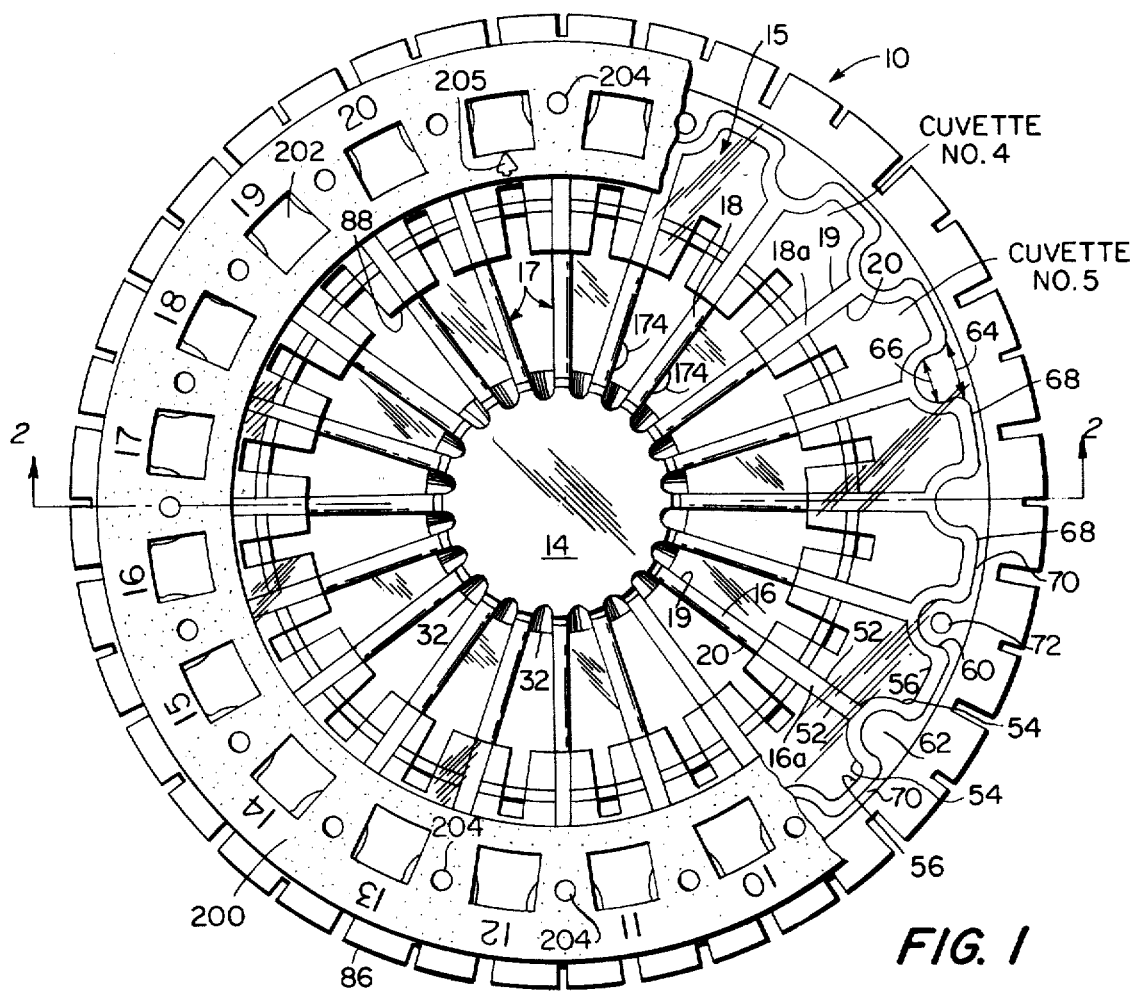
FIG. 1 is a top plan view of the overall assembly of the disc array with a portion of the locator referencing ring broken away.

Referring now to the drawings and initially to FIGS. 1 through 5 and 8, the integral, disposable cuvette array, being generally disc shaped, is designated in its entirety by numeral 10.

As described above, the cuvette array is formed from a preferably optically transparent, flexible, plastic material. The plastic material from which the array is manufactured may be made as thin as possible, so long as the rotor holder for the disc will function in conjunction therewith to prevent the disc from becoming overly distorted or broken during the contrifugation run which is conducted for purposes of analysis. It is to be understood that the material of the array is sufficiently flexible so that some stretching thereof along radial lines would occur if no restraining means are utilized during the analytical centrifugation runs. As explained hereafter, this is prevented by a vertical wall of the rotor which is used as a rotatable carrier for the array during centrifugation. The overall strength and rigidity of the array is also determined and increased by the use of additional ridge lines or walls 17 which form a part or parts of the configurations described and disclosed in detail hereafter.

Basically, the cuvette array has a first, fluid chamber part 12 which has a relatively horizontal hub member 14 from which radiate a series of cuvettes 15,15 in side-by-side relation to each other. Adjacent cuvettes are separated by wall members 17,17 each having an integral top wall 18, and side walls 19 and 20, the side wall 19 forming a portion of cuvette No. 4 (of a total number of 20 cuvettes in the array of FIG. 1) with the side wall 20 forming a portion of adjacent cuvette No. 5. The horizontal top wall 18 and the side walls 19 and 20 are integral and are shaped during a molding or die pressing forming process utilized to produce the part 12, this part having in each curvette 15 a bottom wall 23 with vertical radially extending integral slots 16,16 formed from the side (19 and 20) and top (18) walls and adding rigidity to the array.

Each of the cuvettes 15,15 has an inner compartment 30 defined by two side walls shown at 19 and 20, there being positioned at each of the cuvette rear portions 21,21, generally vertical (inclined) hub inner walls 32,32 which are integrally united with the hub flat portion 34

14 and with the side walls 19,19 and 20,20 and with a thin bottom compartment wall 36 having generally horizontal surfaces, the upper surface being designated as 37, and the bottom surface as 38, each cuvette 15 having this bottom compartment wall 36. Compartment inner walls 32,32 integrally connect the hub flat portion 14 with the compartment 30, the walls 32,32 being inclined forwardly at their lower portions 35,35 in order to better direct fluid flow. Formed in a ring of generally circular shape during the molding operation completely around lower surfaces 23,23 of part 12, and positioned slightly radially outwardly of the center thereof, is a groove 40 which extends upwardly so as to form an inclined ramp wall 42,42, one for each compartment, and radially outward vertical outer walls 44,44, said groove adding rigidity to part 12.

Figure 8:
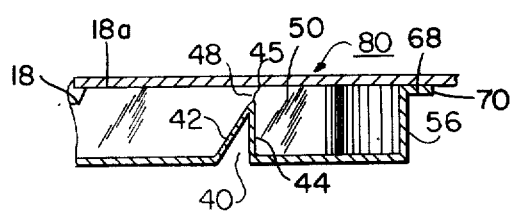
FIG. 8 is a partial view in cross section of the dividing ramp wall taken on the lines 8-8 of FIG. 5 with the rotor holder removed.

As is shown in FIG. 8 particularly, ramp walls 42,42 are inclined at an angle to the vertical. This angle of inclination generally will lie within the range of 45° to 60°. The ridge-like tops 45,45 of ramps 42,42 teminate in each of the cuvettes at a level so as to leave a clearance or passageway 48 between the tops 18 of each of the adjacent pair of side walls 19 and 20.

Radially outward from each vertical wall 44,44 is a second compartment or chamber 50 for each of the cuvettes, the radially inner or back walls of chambers 50,50 being formed by the walls 44,44. The radial side walls 52,52 for each second or outer chamber 50 of each cuvette 15 are formed as extensions of the radial lines of side walls 19 and 20. In order to produce rapid vortexing or mixing motion during the centrifugation run the side walls 52,52 are each curved reversely inwardly to form arcuate walls 54,54 which terminate in a substantially vertical end wall 56, one for each cuvette 15,15.

On the outside of the semicircular portion 60 there is thus formed a pocket or recess 62, which has a width 64 at its outermost point which is slightly greater than the width at the midpoint of the recess, as shown at 66,66. Flat upper walls 68,68 are formed on each of the outer chambers 50,50, preferably by the clamping action of the forming dies while the cuvettes 15,15 are being depressed, or otherwise formed, in the molding operation. The pockets 62,62 are in direct communication with slots 16a formed by extension side wll 52,52. The end top surfaces 18a of each outer chamber dividing member are slightly higher than the top surfaces 18,18. As indicated by the downwardly directed portions 67,67, these elevated portions 18a continue radially inwardly past the tops 45,45 of ramp radial dividing means 42,42.

Positioned outwardly beyond the end walls 56,56 there is a small circular flat rim portion 70 which forms the extreme outer annular portion of the member 12, rim 70 having the same elevation as the tops of walls 56, 52, and the radially outermost elevated portions of top walls 182.

At the center of selected notches or pockets 62, 62 there are formed in the top walls 68,68 protrusions, or projections 72,72.

In the preferred embodiment, there are four of such projections 72 spaced 90° from each other.

As explained in detail hereafter these notches are utilized as accurate registration means, being geometrically fixed relative to the cuvette chambers, since they are spatially positioned in integral fixed relation thereto and are preferably integral therewith.

Figure 2:
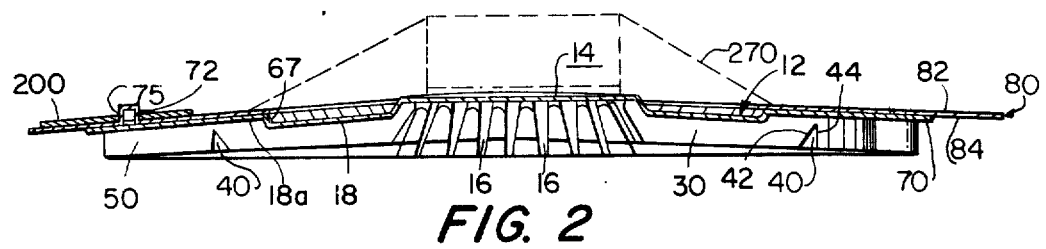
FIG. 2 is a view in vertical cross section taken on the line 2—2 of FIG. 1 and showing the hub portion flexed upwardly.
Figure 11:
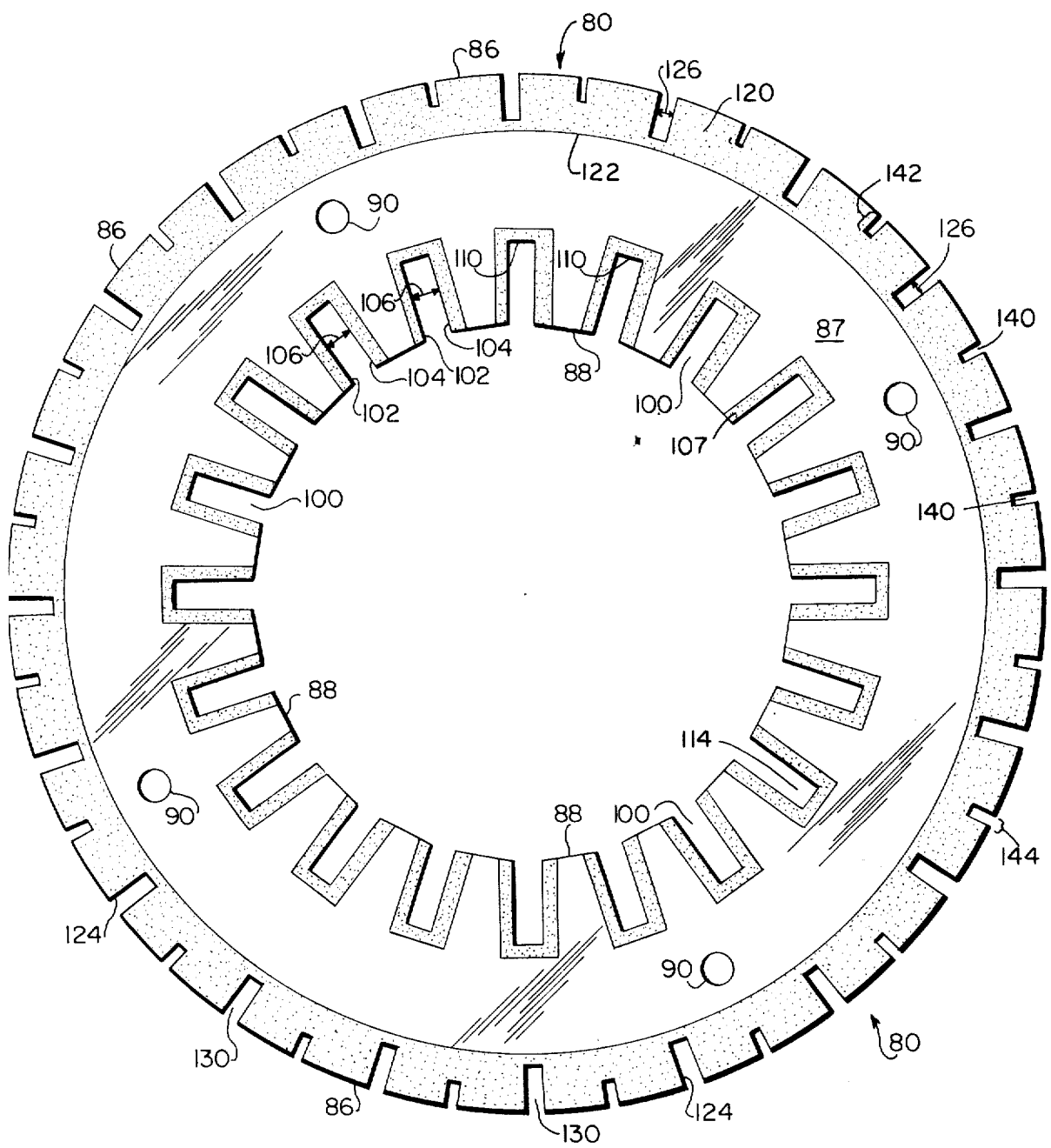
FIG. 11 is an enlarged plan view of the annulus of the array before integral fusion bonding.

Referring now to FIG. 2 and 11, it will be seen that there is a second basic portion of the integral, disposable cuvette disc array, this second portion being of generally flat annular shape and being designated in its entirety by the number 80. As shown in the various embodiments, this member 80 is a substantially horizontal annulus having a generally flat upper surface 82 and a generally flat lower surface 84 extending between a circular outer edge 86 and a circular inner edge 88.

Referring to FIG. 11 positioned in the wall portions 87,87 of the annulus are locating or registration means 90 for coaction with the registration projections 72 extending upwardly from member 12, these being preferably equal in number so that there are one or more sets of locating means on members 12 and 80 coacting together to fixedly position these members. Such locating means may consist of circular passages cut entirely through the thickness of the annulus 80, leaving an opening 90 which is of slightly greater diameter than the top of projection 72. A careful examination of these protrusions 72 will show that their vertical walls 75,75 (FIG. 2) are preferably tapered outwardly in the downward vertical direction so as to have a maximum outer diameter at the bottoms of these walls 75,75 thereof, which diameter is chosen so that it will bind frictionally with the openings 90,90 to fixedly position the annular member 80 relative to member 12. Alternatively, the annulus may have projections extending upwardly which will frictionally bind in coacting mating relation with the side walls 75,75 of the protrusions 72. In either form the recesses 90 must be of sufficient diameter so that the lower surface 84 of the annulus 80 can be joined by fusion, or by other suitable, fluid sealing producing means, to the upper outer surface of member 12 formed by the thin annular ring of flange 70 and upper notch walls 68,68 in fluid sealing reation thereto. The annulus 80 will also be joined to the radially outward upper surface 18a of the cuvette division walls in fluid sealing relation thereto. Accordingly, the annulus 80 is geometrically positioned in fluid sealing relation with the outer portion of the individual cuvette outer chambers 50,50 and with the outermost portion of the inner cuvette chambers 30,30.

Formed in annulus member 80 at the inner edge 88 thereof is an annularly disposed series of radial slots 100, one for each cuvette. The slots are formed by removal of material from the annulus member 80 and are cut or otherwise formed so as to have their side walls 102 and 104 positioned a distance apart equal to that shown at 106,106, this distance preferably being equal for each of the cuvettes. Preferably their edges are outlined with an opaque paint 107 paint or the like to aid in visual identification of the slot. It will be seen that the forwrd or radially outward portions of each of the slots 100,100 end in walls 110,110, one for each cuvette and thus leave openings 114,114, one for each cuvette, each of which provides a passage into its associated outer chamber 50 for insertion of a pipette, syringe, or the like for the deposition in the cuvettes' outer chambers of materials in the form of reactants, or reagents, or unknown samples, such as blood, in these outer compartments 50,50. The inner cuvette compartments 30,30 have the major radially innerportions of the slots 100,100 positioned thereover, so as to allow entrance into each inner chamber 30,30 of a pipette or other dispensing means for desposition therein of materials such as reagents or reactants which may vary from compartment to compartment in composition, depending upon the particular reaction or test desired.

In the normal use of fast centrifugal analyzers, known reagents for a desired specific test are generally positioned within these inner compartments. They may be, if desired, dried or lyophilized, so as to form a soluble coating on at least the lower surfaces 36,36 of the individual cuvette inner chambers 30, 30; if this is done, then the disc need not have additional reagents added thereto prior to or during the analysis run, since either pure water or buffer solution, the latter being properly chosen for the specific desired test, may be added to the inner chambers 30,30, preferably at the sloping hub walls 32,32 to better direct the flow of the added diluent or dissolving fluid.

The outer compartments 50,50 generally have the unknown sample, such as blook or other body fluid, added thereto in the proper amount. This sample addition may be made to as many cuvettes as are required to run the programmed tests.

It will be understood that the amount and composition of the materials placed in each of the inner cuvette chambers which are utilized may be the same for each cuvette 15,15 both as to amount and composition, if the same test is to be conducted in each cuvette. However, frequently a different test will be conducted in each cuvette which is used. In the latter case it is necessary of course, to add reagents of differing compositions and/or amounts to the inner chambers 30,30. Additionally, the amount of materials added may differ from cuvette to cuvette in a fixed relation so as to obtain dilution series results, as is well understood in the art. However, the combined volume of the fluids contained at rest in each cuvette, i.e., the combination of the amount initially in any given inner chamber 30 and the amount in its aligned outer chamber 50 should, if possible, be known and may be the same for each cuvette, so that there will be elimination of variations in optical density readings taken through the optical path due to variance of the thickness of the vertical layer of mixed materials located against wall member 56. Preferably the outermost ring 120 of the annulus 80 is made opaque between the outer annulus edge 86 and a circular line designated as 122, located radially inwardly from edge 86 and from the cuvette outer walls 56,56.

Spaced with one of its edges 124 radially aligned with the cuvette associated therewith is a notch 130 having a fixed width 126. Such notches are positioned radially around the annulus, each slot 130 having the same positioning relative to its cuvette, each notch 130.130 preferably having the same width 126,126 and being spaced geometrically fixedly relative to the remaining members of the disc array. One of these notches, as indicated at 134 in FIG. 7, may be longer in an inner radial direction than any of the others. This will produce transmission of a greater amount of light when positioned to intercept an encoder reading means. It therefore may be used as the beginning, or indexing notch, during rotation of the cuvette array while it is being centrifuged. This slot may be used to measure rotor speed, as well as signalling the start of a new rotation of the array. However, as shown in FIG. 11, the notches 130 extend inwardly the same radial distance. In this case, a separate locator ring, as described in more detail below, is utilized to establish one of the notches as an indexing notch.

Positioned substantially opposite the remaining cuvettes are the other notches 130 used for the formation of encoding pulses by transmission of light.

Also positioned around the peripheral edge 86 of the annulus member 80 are a series of equally spaced smaller notches 140,140 each having smaller but preferably identical depths 142,142 and smaller but preferably identical widths 144,144, Each slot 140, 140 is positioned approximately aligned with the centerline of the dividing walls between the cuvettes, i.e., on a radial line with the center of top wall 18 and projection 72, for encoding purposes.

By the structure thus far described it will be seen that there is produced an inexpensive, disposable multicuvette disc array formed of two integrally united members which members carry thereon the entire encoding means and optical path intercepting cells used with fast analyzers.

Figure 5:
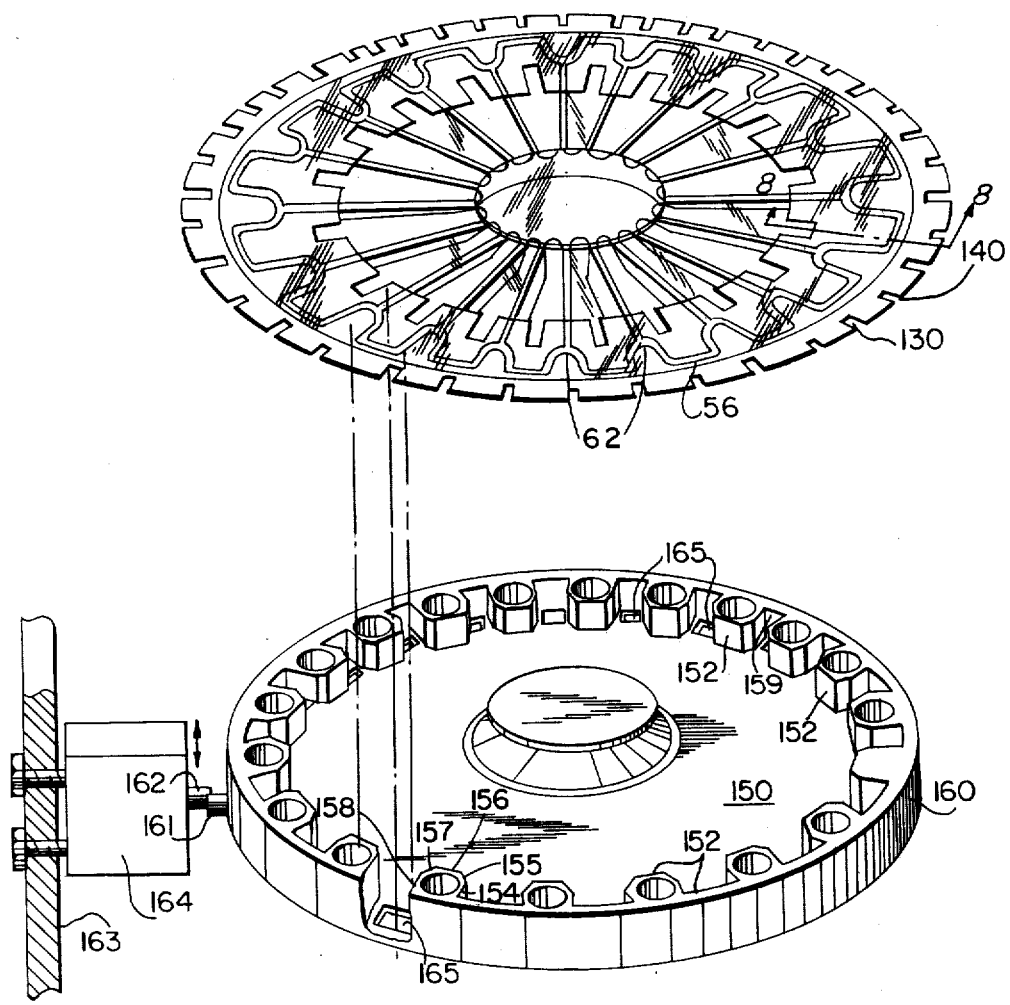
FIG. 5 is a view in perspective of the disc array with its recesses and cuvettes aligned axially and radially and spaced from and above the supporting rotor in which it is adapted to fit in fixed alignment in centrifugation runs and also showing the coacting means on the frame of the analyzer with which the cuvette array is adapted for use and the vertically reciprocable frame mounted stop member used to index the rotor angularly aligned fixedly with the disc cuvette array.

In use, this array has its notches or recesses 62 aligned with inward projections carried by a rotor 150, as shown in FIG. 5. The diameter between the side walls of this rotor will be only slightly larger than the maximum diameter of the cuvette array when at rest, so that the array may fit snugly therein. During rotation, the cuvettes may tend to be stretched radially under the applied centrifugal force, but such stretching will be prevented by the contacting support of the end walls 56, 56 of the cuvettes 15,15 with the inner wall 159 of the rotatable carrier 150. The projections 152,152 extending inwardly also are adapted to snugly fit each corresponding outer wall notches or recesses 62,62 to provide resistance to radial stretching and to accurately position the cuvette array 12 radially with its intended carrier 150. This also serves to prevent relative radial and axial misalignment occurrence during the analytical centrifugal run.

In use, one of the cuvettes will be selected as the start or reference cuvette. Generally it will be filled with water or buffer solution so that the optical density value of a fixed intensity, fixed length light path intercepted by the fluid vertical layer centrifugally held against its outer wall 56 will represent both the start of a rotation of 360° during centrifugal test running and also will give a reading which sets the maximum or 100 percent light transmission characteristic of the cuvette array and is used as a reference.

It will be understood that the cuvettes in the array structures 10 of the invention form a round, generally disc shaped array of horizontally uniformly disposed, integral units which are disclosed in detail above and hereafter, and are generally utilized in so-called fast analyzers. In such systems there are positioned within the array the necessary samples, or standars, which coact, as by chemical reaction, with a chosen set of one or more reactants or additives, there generally being a much greater volume of the fluid of the chosen set than that of the sample, in order so as to produce the desired change in opacity by reaction or pH adjustment or other appropriate means generally designated as a diagnostic analytical test.

The opacity, usually described in terms of optical density or adsorbance, is preferably quantified, so that users of the cuvette array and its associated operational mechanisms and control structures and circuitry therefor will receive, preferably printed automatically on a cuvette associated card by a small printer, highly accurate and reliable information upon which to base the prognosis of a physical condition of a patient, for example, or to accurately monitor the environmental effects, or to determine the maximal output decision, or are provided with sufficient information to enable them to display a profile of the analog of the individual cuvettes, thus determining the rate and direction of the reaction.

Various algorithms such as ratiometric, two-point ratiometric, rate-ratiometric, or kinetic programs may be run with this array.

Thus, in a typical biochemical analytical programmed procedure the outer annular series of chambers 50,50 will be loaded with, for example, ten microliters of serum or the like, while the inner chambers 30,30 are loaded with a sufficient amount of reactants and a diluent therefor such as distilled water, these mixed materials being added by manual or automatic pipetting and in a much greater amount, e.g., 170 microliters. It will be understood that these amounts are not great enough to cause the fluids in the cuvette chambers to overflow when the cuvette array is stationary. There is little possibility of leakage between the two main members 12 and 80 or at any joint, particularly because the fusion bonded joint which unites the sheet member 12 to the flat annulus 80 prevents leakage.

Figure 6:
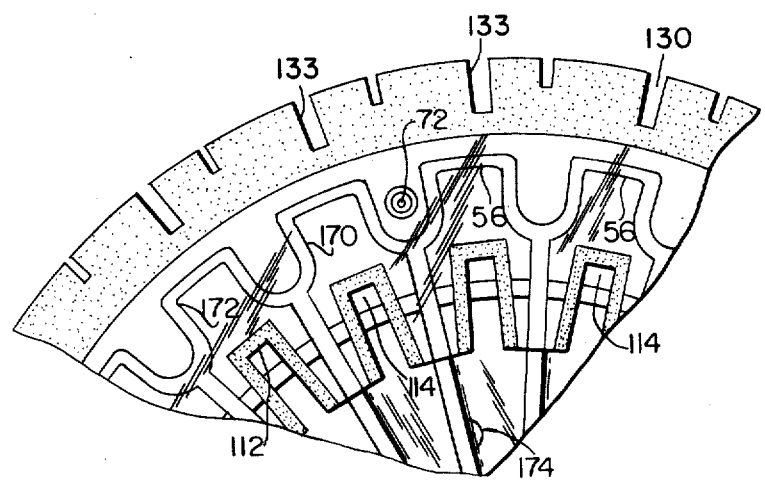
FIG. 6 is a plan view of a blown-up portion of the top outer array portion showing the opaque markings thereon in detail.

During centrifugation the liquid contained within the inner chambers is forced outwardly at a relatively initially high rate of speed due to the rapid rotation of the support means, or rotor carrier 150 with which the cuvette array 10 is adapted to be functionally fixedly associated, so far as spatial relations are concerned. The rotor and the cuvette array may, for example, during an initial mixing cycle, have a speed of between 2,000 and 5000 rpm, preferably between 4,000 and 5,000 rpm. This centrifugal pressure in the generally radial direction causes the fluids in chambers 15,15 to climb over the ramp portion 42 of annular dividing wall 40 and to pass through the passageway 48 defined by the lower part or surface of annulus 80 and the side walls 19 and 20 and the bottom wall 23 of each cuvette. It is at this point that the fluids and contained molecules of the solution begins to be mixed and take part in a swirling motion during this mix cycle. In order to prevent the direct force centrifuged fluids from high level impacting at one or more circumferentially outward points which, if the rotation is clockwise, will occur a the side shown as 170 (FIG. 6) at the portion 172 therefore, where the annulus 80 is fusion bonded on its lower surface 84 to the outer flange member 70. This flange 70, as described above, is a thin annulus positioned radially outwardly of the outermost ends of the cuvette chambers and their structures. To minimize destructive impact, there are provided the abovedescribed reversed, inwardly curved wall portions 54 which force the liquids flowing outward to be diverted toward the cuvette centers. This minimizes the pressure at the fusion joints. There may also be provided additional fluid diverting lateral extensions or protrusions of the walls of the cuvettes, such as shown at 174 in FIGS. 1, 6 and 7. These further prevent maximum impact of the centrifuged material against outer wall 56, preventing bursting or undue strain on the thin flexible plastic cuvette arrays of the present invention.

The opaque encoder outer portion 20 has positioned thereon as encoding indexing and synchronization means two sets of slots 130 and 140 described above. Therefore, as the array rotates, each of the slots 140 will transmit light for a time determined by the width of the slot, which is giometrically, spatially related to its adjacent cuvette, and by the rotary speed of the cuvette array. The value of these uniform light transmissions is determined by photocells or photodiodes located adjacent the slots. This gives a series of pulses, each substantially uniform, while the value of the opaque area forms the dark current read value which feeds a cuvette analyzer. Hence, the dark current level reference for each cuvette is automatically adjusted by the size and geometric positioning to produce slot pulses which compensate for both transient and steady background errors just prior to the adjacent cuvette absorbance reading.

During the analytical run, following the initial high rotor mixing speed, the cuvette array will generally be slowed to a rotary speed of about 600 rpm.

By reliance on geometric spatial determination of the width and length of the encoding slots 140 and in the same manner fixing their distance from the read areas individually for each cuvette just prior to cuvette optical transmission measurement, there can be virtually no possible error introduced by the cuvette array. If the encoding slots are placed on the rotor supporting the array, as in the prior art, or on a separate disc carried by the rotor shaft, permanent or transient misalignment of the encoder slots relative to the cuvette read area may occur, thus greatly diminishing reliability and uniformity. The cuvette arrays of the present invention have vertical outer walls which closely fit, but do not frictionally fit, at rest, the inner vertical walls of the rotor. While a series of radially spaced arcuate notches are adapted to coact with a series of almost semicircularly shaped inwardly directed, similarly spaced rotor projections, it is to be understood that this mating geometric relationship may be of a sinuous configuration, or of a rectangular configuration.

As can be seen in FIG. 5, the projections 152 of the rotor 150 may be formed from a series of angularly related planar surfaces such as shown at 154,155,156,157,158 extending inward from vertical circular wall 159. Positioned on the vertical outside wall 160 is an index stop member 161, coacting with a vertically adjustable stop member 162 connected to a fixed reference frame 163 by connection means 164 to stop the rotor from rotation when it and the cuvette array are to be initially aligned, so that annular optical openings 165,165 match the optical areas of the array.

The slight play which is present when the cuvette array is first inserted into the rotor carrier produces no error because, the cuvette array and its rotor support, once mated and assembled, are fixedly held by a vertical clamping force (by means not shown) applied to the array to prevent relative motion between array and rotor. The centrifugal force also causes a slight stretching of the thin plastic, flexible material of the array, radially and in a curved radial path, further preventing error by relative shift.

The same geometrical prevention of error is also accomplished by the broader and lengthier encoding slot series synchronization slots 130,130, uniformly spaced around the opaque outer integral flange of the array annulus. These slots are preferably positioned with their left edges 133 in registry with the optical path areas of the individual cuvettes, the cuvette light path area being about on square cm (see FIGS. 6 and 7). This is to produce uniformly spaced synchronization pulses with uniform duration by geometrical configuration.

Figure 4:
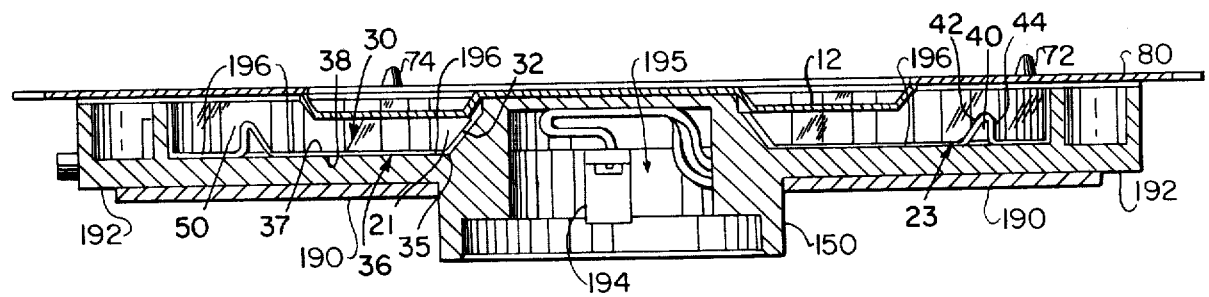
FIG. 4 is a view in vertical cross section of the disc cuvette array positioned indexed in fixed relation substantially horizontally within the rotor which coacts with and rotates the array during an analysis run.

Referring to FIG. 4, it will be seen that the rotor carrier 150 for the cuvette arrays of the present invention has a flat heating annulus 190 on its lower surface 192. The rotor is preferably formed of aluminum or other substantially rigid heat conducting material, so that it forms a thermal mass for fine, instantaneous heat adjustment of the cuvette array, by measurement with a transistor or the like 194 at or near the center 195 of the rotor. Electric lead lines may project downwardly into a rotor drive shaft equipped with slip rings. The upper rotor surface 196 is substantially flat so as to produce maximum contact with all of the lower wall or bottom wall portions of the cuvette array. Since the disc array is thin and flexible, its bottom portions 23,23 will mate with the upper wall of the rotor. It is thus adapted for insertion into the rotor with close thermal contact with the rotor surface throughout its lower bottom wall areas, even if the bottom walls and/or the upper wall of the rotor are uneven initially. This disc flexibility thus ensures that the analysis cuvettes will all remain substantially perpendicular to the fixed read optical path, and is enhanced as to stability and reproducibility by the aid of the built-in inherent snap bias discussed below.

This is not true of the prior art arrays. These are either totally rigid or have an extremely limited flexibility; in either case, a magnified view will show that, in essence, the array cannot reach or maintain close contact with the rotor surface, but rather sits on a very large series of tiny rotor surface projections, at best reducing thermal contact to a point-to-point system usually having less than one-half the contact area which the present invention arrays are formed to provide. Heat transfer is enhanced, of course, by the thinness of the array bottom flexible wall.

The array may be formed of any material inert to the materials to be contained therein, such materials as polyvinyl or polyvinyledene polymers or terphthalates, etc., preferably having a light transmission of at least 35% at 3400 Angstroms. Since most systems use the first cuvette as a measurement of maximum transmission with either no water, or distilled water or the diluent being placed in this cuvette, a similar use may be made of the second cuvette.

Figure 7:
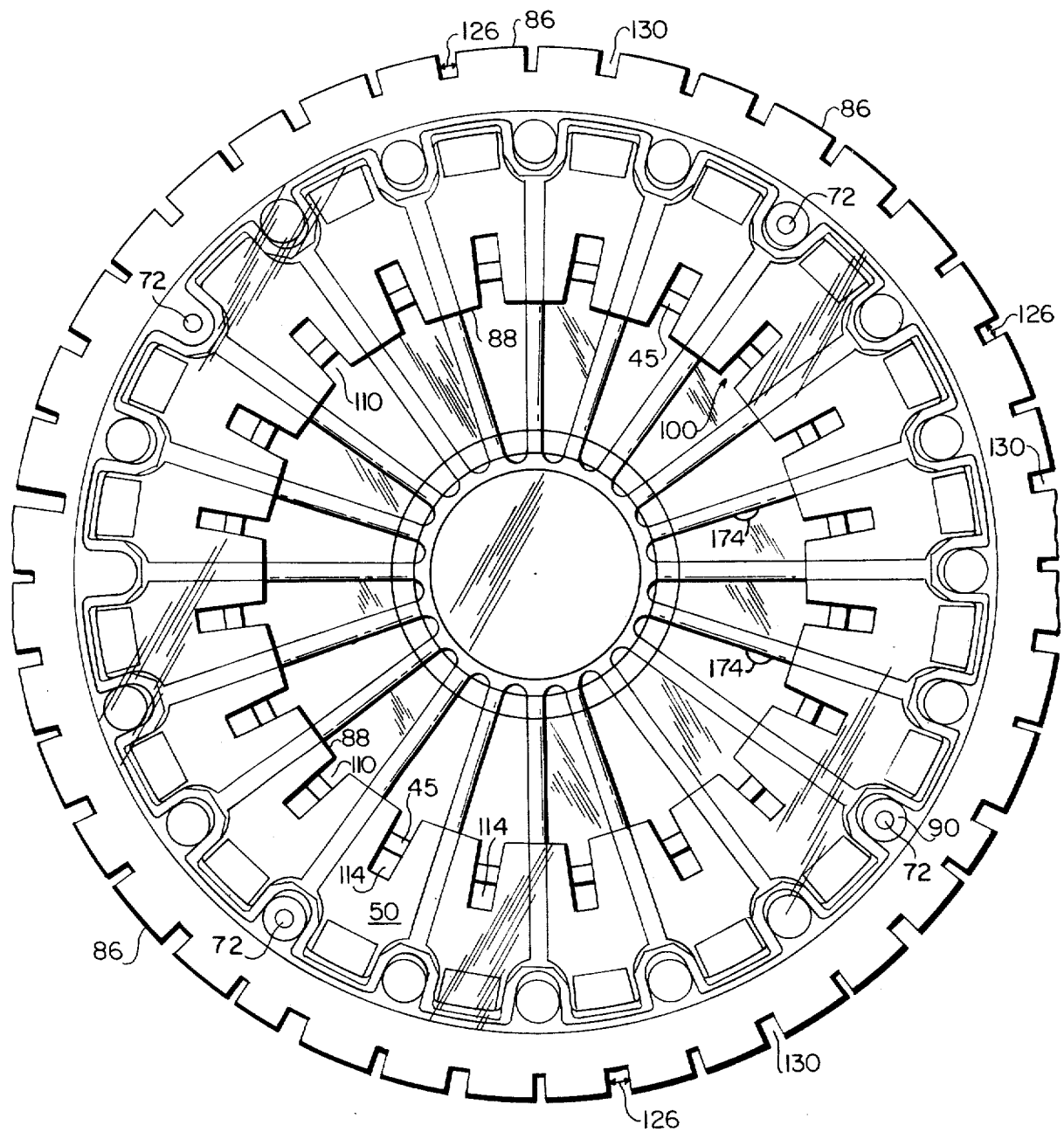
FIG. 7 is a top plan view of a modified form of the cuvette array disc located within the rotor holder for use with which it is adapted with the identifying ring removed.

If a predetermined, geometrically fixed cell is to be the indexing first cell measured in each complete rotation of the array, then the geometry of slots 130 may take the form of FIGS. 7 and 16 wherein slot 134 is longer and/or wider than the other slots in the sync set.

If non-uniform or special encoding slots are to be used, then the flange 120 is unslotted, as shown in FIG. 14. The customer may be provided with a punch to produce the slots desired.

The most preferred and versatile embodiment, however, is that shown in FIGS. 1, 7 and 11, wherein all of the pulse slots 130 initially have the identical width, radial spacing and length. This produces, especially if combined with an indexing upwardly projection between each adjacent pairs of cuvettes, a means whereby any cuvette can be made the number one cuvette which generates a speed reset pulse once for ech rotation.

Figure 12:
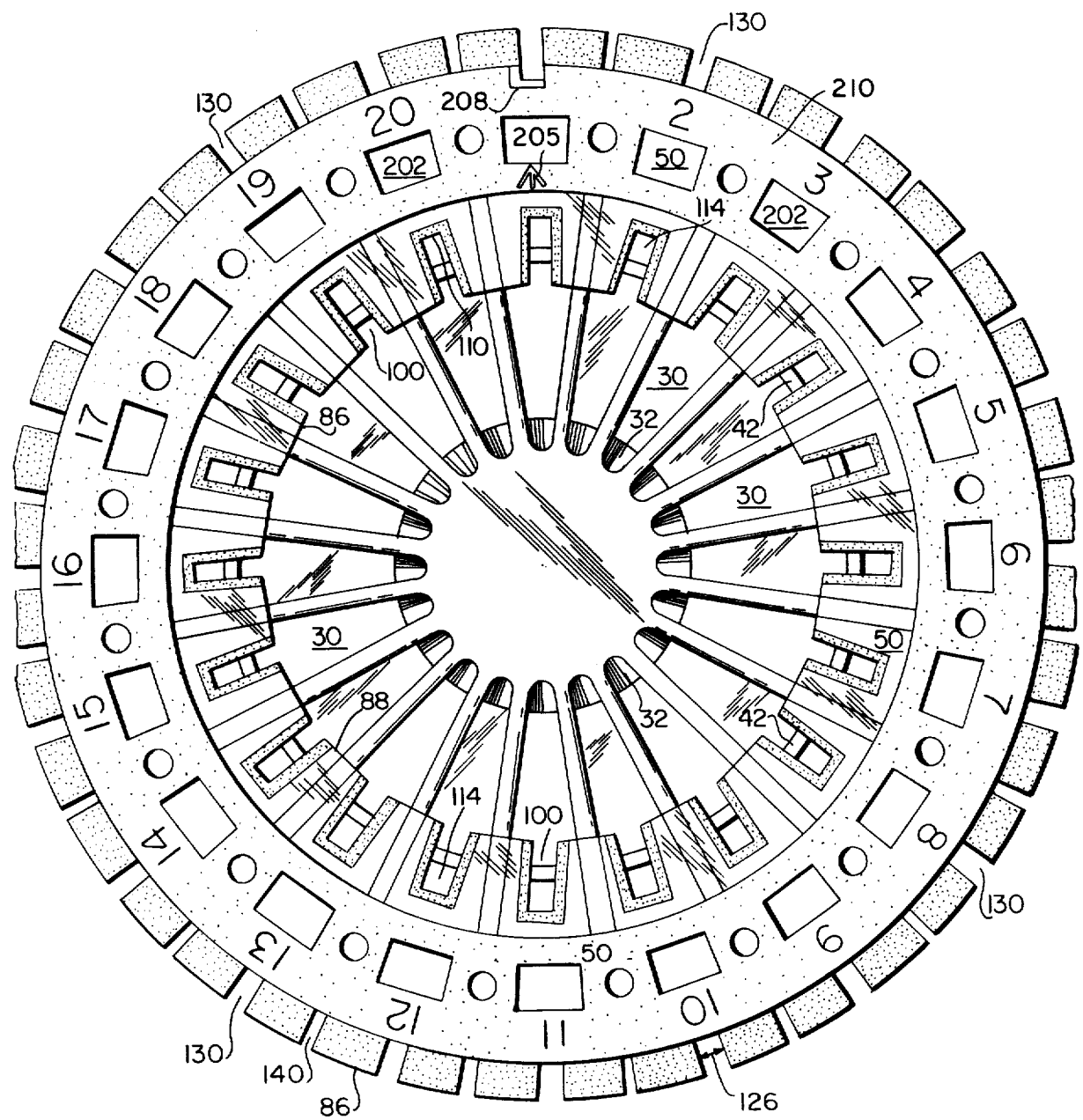
FIG. 12 is a plan view similar to FIG. 1 showing the entire locator ring in its run position.

As best seen in FIGS. 1, 12 and 15, a separate opaque indexing or locator ring, or annulus 200, is provided. It has windows 202,202 formed therein, preferably of rectangular shape to allow an unhindered optical path through the measured area of the outer portion of each cuvette.

The ring may be seated removably over the array with the start cycle arrow 205 thereof pointing to any cuvette by relatively rotating the ring and dropping it so that the projections 72 pass through holes or passages 204,204 or other mating means of which there may be one opposite each wall between adjacent cuvettes, or the selectivity may be reduced as described above with pairs of registering passages coacting with pairs of projections.

The ring slot 208 opposite the arrow does not cover the inner parts of selected slot 130, but the radially inner ends of all the rest of slots 130 are covered by the outer portion 210 of the ring, so that only one slot is longer than the rest.

In the prior art, the arrays, even if plastic, have been thick and expensive, and usually made by fine precision machining. Hence, they must be reused, so that if only, e.g., three cuvettes thereof are used, the entire array must be carefully washed, usually repeatedly, before reuse. This requires an expensive and space-consuming wash station and lengthens the overall complete analysis cycle by a large factor.

The present invention allows ready array reuse, using the cuvettes not previously utilized in the first run. This is readily apparent from FIGS. 1, 12 and 15. For example, the first run may use cuvettes 1 and 2 as references, with tests in only cuvettes 3 and 4. To use the same cuvette array for a second run, the annular locator or indexing ring 200 is lifted off the array and rotated relative thereto before being repositioned. In FIG. 15, the locator ring 200 is positioned with the initial cuvette slot 208 registered with cuvette 5. Ring 200 has indicia 206 and array 10 has indicia 207 to aid in cuvette location.

In this fashion, the array can be utilized a plurality of times. The new starting cell need not be the first adjacent cuvette not previously used; it may be any unused cell.

Instead of using reagent adding slots which communicate with both inner and outer chambers of the radially disposed cuvettes, there may be provided in integral annulus 12 a series of holes 220 as shown in FIG. 11 to communicate with outer chambers 50. Also, more than one annular dividing wall may be used.

Figure 10:
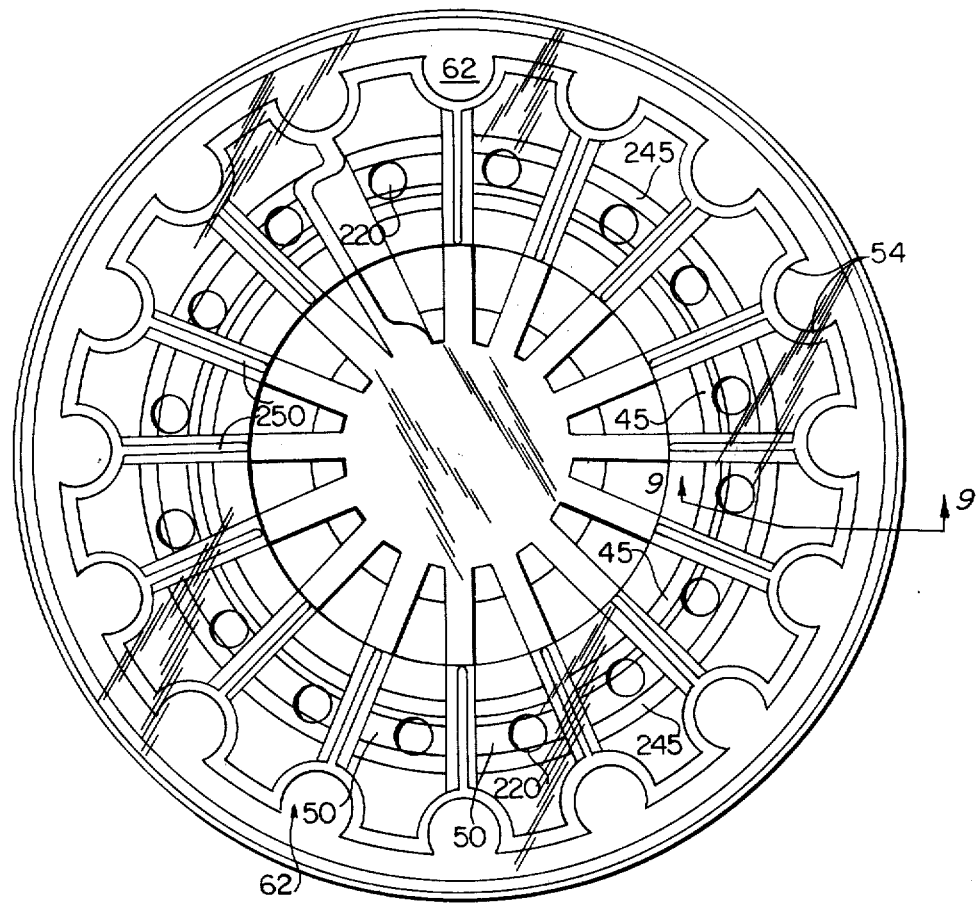
FIG. 10 is a plan view of an alternative array with holes replacing the slots.
Figure 9:
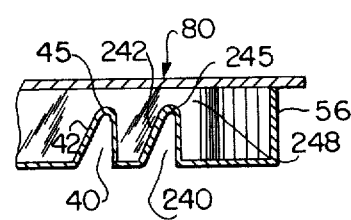
FIG. 9 is similar to FIG. 8, and shows an alternative embodiment having three compartments and two dividing ramp walls; it is a section of the array shown in FIG. 10.

FIGS. 9 and 10 show this structure with annular slot 240, ramp 242, top 245 and passage 248 serving as the second series of dividing means. Also shown are radial reinforcing ribs 250.

Figure 3:
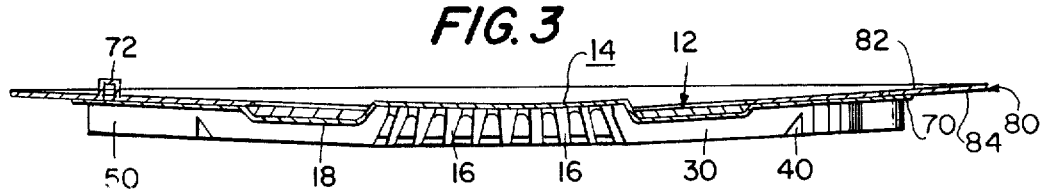
FIG. 3 is a view similar to FIG. 2 showing the hub portion flexed downwardly.

Referring now to FIGS. 2 and 3, as stated above, the integral array is formed during molding with more material placed near the center than the outer edge so that the flexible array has a built-in bias pressure. Thus, downward force exerted at the flat hub portions 14 will force the hub down if the array is seated in a rotor carrier or is clamped at the annulus. After the central portion has passed the horizontal mid-point of its travel down to the lower position shown in FIG. 3, it will be clamped by a cap 270 which holds it against the rotor more firmly, since the hub is trying to push itself down and thus enhances the thermal contact. The cap 270 used for this exertion of strength will also serve as a sealing member, since the cap (as shown in dotted lines in FIG. 20 will cover from the hub center past the ends 110 of these slots without causing appreciable deformation of the upper array structure.

Figure 13:
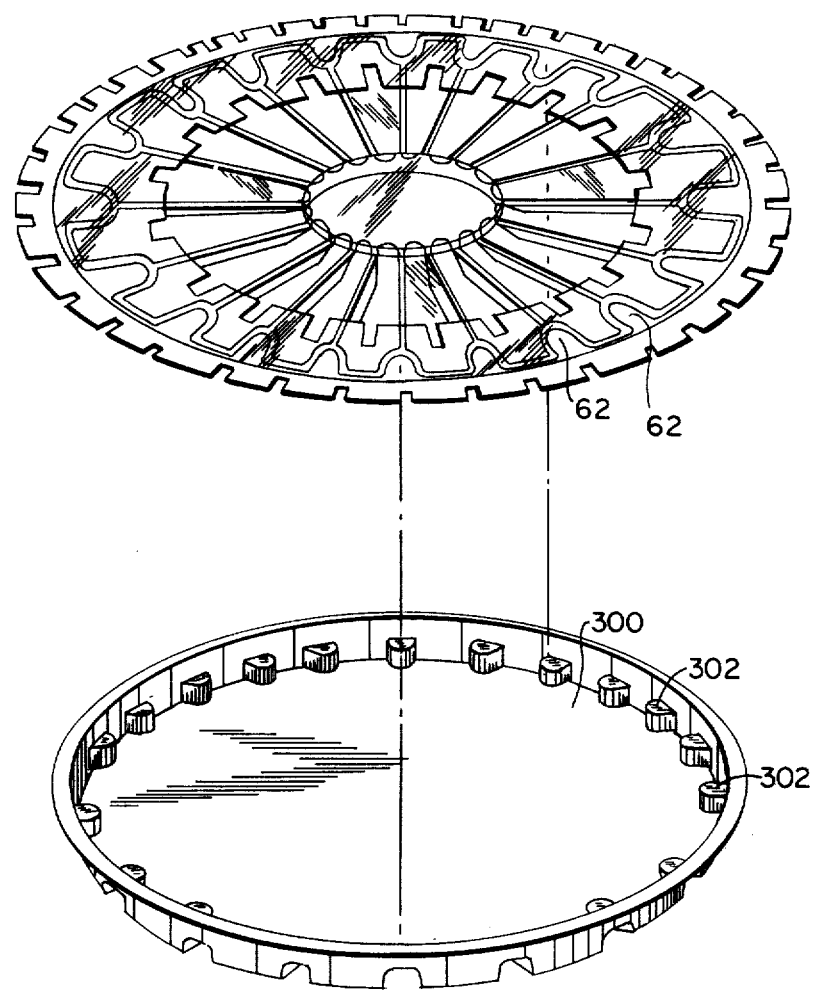
FIG. 13 is a perspective view of the cuvette array positioned above a shipping support and protective disc with which it is adapted to coact with the array notches angularly aligned with inner indentions found on the support.

The cuvette array is shown in FIG 13 above a shipping support 300. The notches 62 in the array align with indentations 302 in the support.

The array is intended especially for use in systems of the above-listed applications, but may be adapted to most other centrifugal fast analyzers.

We claim as our invention:

1. A cuvette array for a centrifugal analyzer, said array comprising a plurality of compartments circumferentially spaced about a central point, said array is disposable and is formed from upper and lower discs of flexible thermoplastic material, said lower disc is formed with said compartments, and said upper disc is bonded to said lower disc and closes off at least a portion of each of said compartments.

2. A cuvette array according to claim 1, in which said lower disc includes a central hub portion, said compartments extend radially outwardly from said hub portion, and the side walls of adjacent compartments are spaced apart from each other.

3. A cuvette array according to claim 2, in which each pair of adjacent side walls of said lower disc compartments are joined together at least in part by a flat section of thermoplastic material.

4. A cuvette array according to claim 3, in which said lower disc terminates in an outer circumferential flange, and said upper disc is bonded to said flat section and said flange of said lower disc.

5. A cuvette array according to claim 4, in which said outer circumferential flange and said flat section of said lower disc are coplanar, and said upper disc is a flat annulus bonded to said outer circumferential flange and said flat section of said lower disc.

6. A cuvette array according to claim 1, in which said upper disc includes cut-away portions thereof in registry with said compartments to provide for the introducton of fluids into said compartments.

7. A cuvette array according to claim 6, in which said compartments of said lower disc constitute a series of radially inner and a series of radially outer compartments circumferentially spaced about said central point, each radially inner compartment communicates with an individual one of said radially outer compartments, and each of said cut-away portions of said upper disc is in registry with an individual pair of communicating radially inner and outer compartments.

8. A cuvette array according to claim 1, in which the assembly of said upper and lower discs terminates in an outer circumferential flange extending radially outwardly from said compartments and of a light transmissivity varying in portions thereof and used for signal processing purposes.

9. A cuvette array according to claim 8, in which said outer circumferential flange is an outer circumferential part of said upper disc.

10. A cuvette array according to claim 1, in combination with a locator ring removably positioned upon said upper disc in one of a plurality of registered postions.

11. A cuvette array according to claim 10, in which said locator ring has portions thereof varying in light transmissivity that are used for signal processing purposes and to denote a primary one of said compartments.

12. A cuvette array according to claim 11, in which said locator ring includes tabs on the inner periphery thereof used to retain said locator ring against said upper disc.

13. A cuvette array according to claim 11, in which said upper disc includes nipples extending therethrough from said lower disc and removably engaged by said locator ring in one of a plurality of positions for providing variable positioning of said locator ring upon said upper disc.

* * * * *